US012250942B2

(12) United States Patent
Luque Vera et al.

(10) Patent No.: US 12,250,942 B2
(45) Date of Patent: Mar. 18, 2025

(54) ELECTRIC DEVICE FOR DISPENSING VOLATILE SUBSTANCES

(71) Applicant: ZOBELE HOLDING S.P.A., Trento (IT)

(72) Inventors: Sergio Luque Vera, Barcelona (ES); Joaquin Llorente Alonso, Barcelona (ES); Ruben Garcia Fabregas, Barcelona (ES)

(73) Assignee: ZOBELE HOLDING S.P.A. (IT)

( * ) Notice: Subject to any disclaimer, the term of this patent is extended or adjusted under 35 U.S.C. 154(b) by 277 days.

(21) Appl. No.: 15/737,858

(22) PCT Filed: Jun. 27, 2016

(86) PCT No.: PCT/EP2016/064835
§ 371 (c)(1),
(2) Date: Dec. 19, 2017

(87) PCT Pub. No.: WO2016/207433
PCT Pub. Date: Dec. 29, 2016

(65) Prior Publication Data
US 2019/0000064 A1    Jan. 3, 2019

(30) Foreign Application Priority Data

Jun. 26, 2015   (ES) .............................. ES201530921

(51) Int. Cl.
*A01M 1/20*       (2006.01)
*A61L 9/012*      (2006.01)
*A61L 9/03*       (2006.01)

(52) U.S. Cl.
CPC ........... *A01M 1/2077* (2013.01); *A61L 9/012* (2013.01); *A61L 9/03* (2013.01); *A61L 2209/135* (2013.01)

(58) Field of Classification Search
CPC .............. A01M 1/2077; A01M 1/2083; A01M 1/2088; A61L 9/012; A61L 9/03;
(Continued)

(56) References Cited

U.S. PATENT DOCUMENTS 5,647,052 A * 7/1997 Patel .................. A01M 1/2083
                                                     392/390
5,994,677 A * 11/1999 Akerlind ............... A47J 36/027
                                                     219/502

(Continued)

FOREIGN PATENT DOCUMENTS

| CA | 2 931 763 A1 | 6/2015 |
| EP | 1 249 164 A1 | 10/2002 |

(Continued)

OTHER PUBLICATIONS

International Search Report mailed Sep. 7, 2016 in corresponding PCT International Application No. PCT/EP2016/064835.

(Continued)

*Primary Examiner* — Eric S Stapleton
(74) *Attorney, Agent, or Firm* — OSTROLENK FABER LLP

(57) ABSTRACT

An electric device for evaporating and dispensing volatile substances, such as perfumes and insecticides, using thermal energy, that includes a casing and a container of volatile substance detachably coupled with the casing, heating means arranged in the casing for heating the volatile substance, and control means for controlling the operation of the heating means in accordance with a heating program. The device further includes detection means suitable for detecting an intrinsic characteristic of the container and/or the volatile substance, for example, the color of a part of the container, the shape of a part of the container, the container material, or the volatile substance color. The control means (Continued)

execute a specific heating program for a detected intrinsic characteristic.

11 Claims, 3 Drawing Sheets

(58) Field of Classification Search
CPC ...... A61L 2209/135; B67D 2001/0811; B67D 3/0006; B67D 7/344; B67D 7/346
USPC ................................ 392/386, 390, 393, 394
See application file for complete search history.

(56) References Cited

U.S. PATENT DOCUMENTS

| | | | | |
|---|---|---|---|---|
| 7,589,340 | B2* | 9/2009 | Dancs | A01M 1/2077 |
| | | | | 250/577 |
| 2001/0009610 | A1* | 7/2001 | Augustine | A61M 5/44 |
| | | | | 392/470 |
| 2002/0181946 | A1* | 12/2002 | Brown | A01M 1/2077 |
| | | | | 392/390 |
| 2004/0009103 | A1* | 1/2004 | Westring | A61L 9/037 |
| | | | | 422/125 |
| 2006/0193611 | A1* | 8/2006 | Ruiz Ballesteros | A61L 9/035 |
| | | | | 392/394 |
| 2006/0279127 | A1* | 12/2006 | Cronin | A01M 1/2044 |
| | | | | 297/464 |
| 2008/0038156 | A1* | 2/2008 | Jaramillo | A61L 9/03 |
| | | | | 422/123 |
| 2011/0132992 | A1* | 6/2011 | Hoppe | A61L 9/02 |
| | | | | 239/6 |
| 2014/0016916 | A1* | 1/2014 | Lee | F24C 1/02 |
| | | | | 392/309 |
| 2014/0091487 | A1* | 4/2014 | Belongia | A61L 9/122 |
| | | | | 261/146 |
| 2015/0182963 | A1* | 7/2015 | Samper | B01L 3/523 |
| | | | | 422/502 |

FOREIGN PATENT DOCUMENTS

| | | |
|---|---|---|
| EP | 1 790 359 A1 | 5/2007 |
| ES | 2 258 269 T3 | 8/2006 |
| ES | 2 293 593 T3 | 3/2008 |
| ES | 2 300 593 T3 | 6/2008 |
| ES | 2 324 562 T3 | 8/2009 |
| WO | WO 03/014682 A1 | 2/2003 |
| WO | WO 03/077962 A2 | 9/2003 |

OTHER PUBLICATIONS

Written Opinion mailed Sep. 7, 2016 in corresponding PCT International Application No. PCT/EP2016/064835.
Search Report dated Oct. 6, 2016 in corresponding Spanish Patent Application No. 201530921.

* cited by examiner

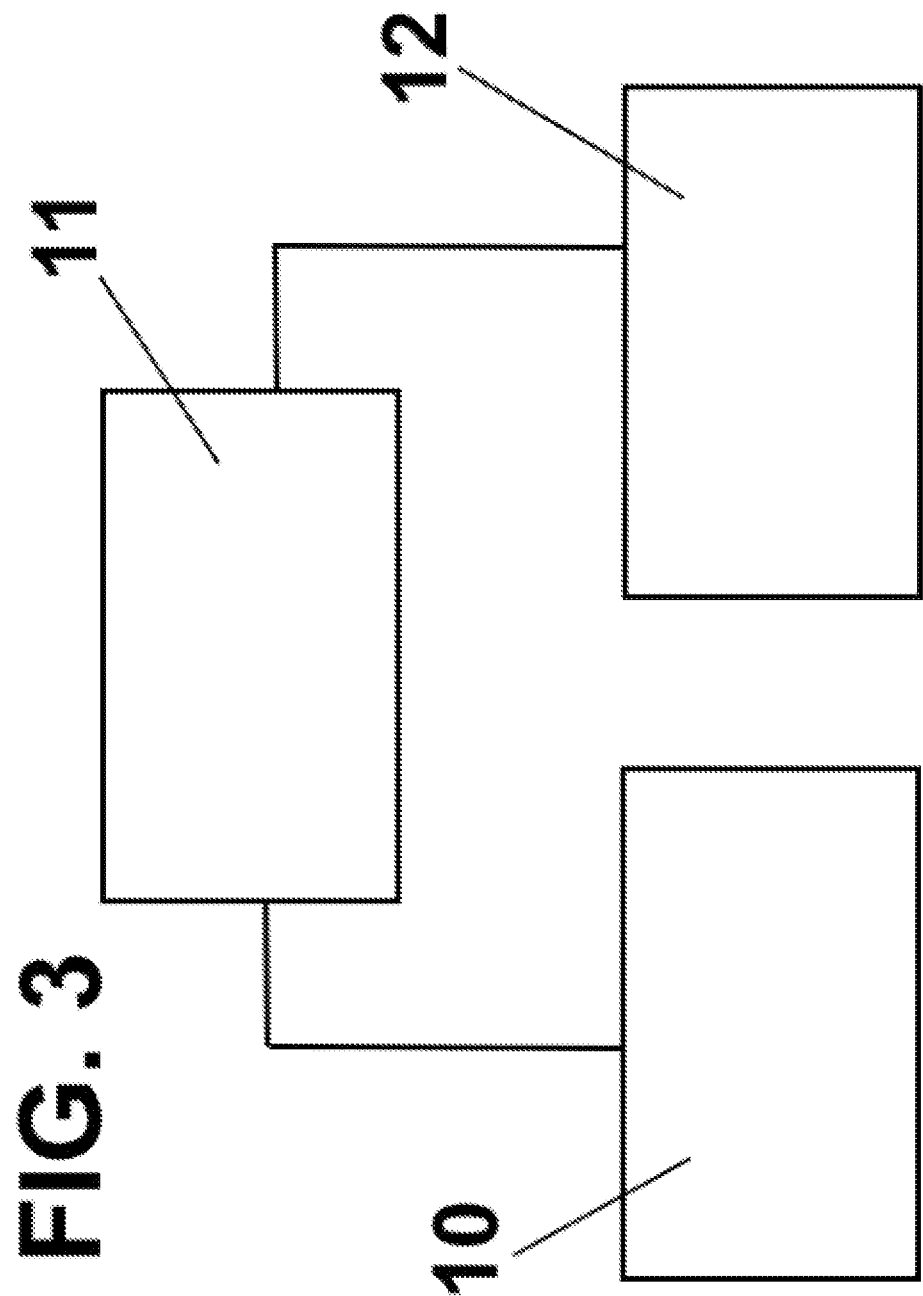

ELECTRIC DEVICE FOR DISPENSING VOLATILE SUBSTANCES

CROSS-REFERENCE TO RELATED APPLICATIONS

The present application is a 35 U.S.C. §§ 371 national phase conversion of PCT/EP2016/064835, filed Jun. 27, 2016, which claims priority to Spanish Patent Application No. P201530921, filed Jun. 26, 2015, the contents of which are incorporated herein by reference. The PCT International Application was published in the English language.

OBJECT OF THE INVENTION

The present invention refers to an electric device for evaporating and dispensing volatile substances, such as perfumes and insecticides, using thermal energy.

An object of the invention is to provide a volatile substances dispensing device, capable of selecting automatically its evaporation settings (temperature and time) for different types of volatile substances, such as the device can operate with different types of volatile substances and several evaporation patterns.

BACKGROUND OF THE INVENTION

There are known many different types of volatile substances dispensing devices, which are controlled electronically such as, the device itself or the user, set evaporation periods and interval to dispense a perfume or an insecticide to the environment.

However, in this type of devices the time settings are established without taking into account the volatile substances composition, and without taking into account the remaining amount of volatile substance, and it may occur that when the volatile substance is finish, the device is still turned on, thus unnecessarily consuming energy.

On the other hand, current electric evaporators operates with fixed temperatures during the entire evaporation periods, so that the volatile substances designers have to find a chemical composition that properly evaporates at a fixed temperature and during a specific time period. Therefore, the current fragrances developments in this field, is complicated and expensive, and the ingredients choice is reduced.

It could be said that in the state of the art, it is the volatile substance and the containers which have to be designed and adapted to meet the working conditions of existing evaporators with a reduced range of operating settings, such as the capabilities of the evaporator, is in fact a limitation for the fragrance designer.

SUMMARY OF THE INVENTION

The present invention is defined in the attached independent claims, and provides an evaporator device capable of automatically setting a specific temperature and dispensing time for a particular type of volatile substance to be dispensed.

According to the invention, a wide collection of fragrances and/or insecticides are provided, and the device includes detection means to detect the type of substance supplied to the device, and to set a specific evaporation setting for that substance.

Therefore, and aspect of the invention is an electric device for dispensing volatile substances, which comprises a casing and a container or refill of volatile substance detachably coupled with the casing. Heating means are arranged in the casing for heating the volatile substance to enhance its evaporation, and control means for controlling the operation of the heating means in accordance with a heating program.

According to the invention, the device further comprises detection means suitable for detecting an intrinsic characteristic of the container and/or the volatile substance, wherein that intrinsic characteristic may consist of: the color of a part of the container, the shape of a part of the container, the container material, or the volatile substance color.

The control means are adapted for executing two or more heating programs, wherein each heating program is adapted for controlling temperature and activation time of the heating means. The control means are additionally adapted to execute a specific heating program for a detected intrinsic characteristic.

The device of the invention detects automatically the refill type and sets a suitable temperature and timing predefined that that particular refill and volatile substance contained therein.

The use of a volatile substance is optimized, since the situation when the refill is not being fully used is solved, and the situation when the device is turned on for too long wasting energy trying to evaporate from empty refill, is prevented.

There is no need to design the chemical composition of the fragrance to work at a specific temperature. Instead, once a fragrance or several fragrances have been freely designed, it is the device which is programmed during its manufacture to operate properly for each type of fragrance. This allows optimal design of the fragrance with relation to cost and ingredients choice.

BRIEF DESCRIPTION OF THE DRAWINGS

Preferred embodiments of the invention, are henceforth described with reference to the accompanying drawings, wherein:

FIG. 3 is a diagram showing the heating means 10, the controlling means 11 and detection means 12.

PREFERRED EMBODIMENT OF THE INVENTION

Figure 1:
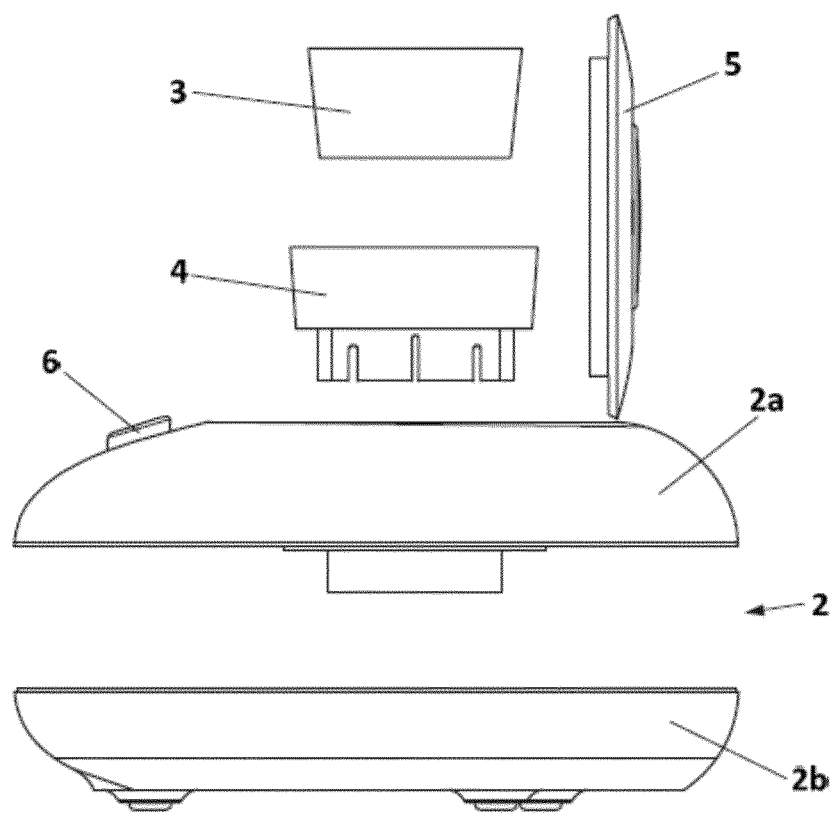
FIG. 1.—shows a an exploded view of an exemplary implementation of the device of the invention.

FIG. 1 shows a preferred embodiment of a dispensing device (1) comprising a casing (2) and a container (3) containing a volatile substance, preferably a perfume and/or an insecticide. The casing (2) is formed by upper and lower parts (2a,2b) permanently attached, and it is configured to rest on a surface. The casing (2) houses heating means 10 arranged for heating the volatile substance, and control means 11 for controlling the operation of the heating means. A switch (6) serves to turn the device on and off.

The container or refill (3) is detachably coupled with the casing (2) for its replacement by a new one once the volatile substance has been consumed. More specifically, the casing (2) has a cavity at it upper part and the container (3) can be inserted in that cavity (3). The container (3) is received within a metallic heat-sink (4), and a grilled lid (5) covers the container during use of the device, for preventing a user from touching the warm container.

The container (3) may be obtained from a thermoplastic material, which may be colored or transparent or translucent partially or completely, such as the color of the volatile substance is visible through said transparent or translucent part. Alternatively, the container (3) is metallic for better temperature transfer.

As per the volatile substance, this can consist of a gel composition or a wax, and a protective foil is provide at an open base of the container, which is peeled off or punched (for example by the lid) for the activation of the container. Alternatively, the volatile substance is a liquid, and a vapor-permeable membrane (9) covers the container open base.

The device (1) comprises detection means or sensor 12 suitable for detecting: the color of a part of the container, the shape of a part of the container, the container material, the volatile substance color, or any other intrinsic characteristic of the container or volatile substance.

In one preferred embodiment, the detection means is a color sensor arranged for sensing the color of a part of the container.

In another preferred embodiment, the container has a transparent area, and the detection means is a color sensor arranged for sensing the color of the volatile substance through said transparent area.

There are different types of color sensors in the market, for example a RGB sensor or a photocell can be used for this application.

In another preferred embodiment, the detection means comprises one or more electric switches arranged in the casing for being activated by a part of the container when the container is coupled with the casing.

Figure 2:
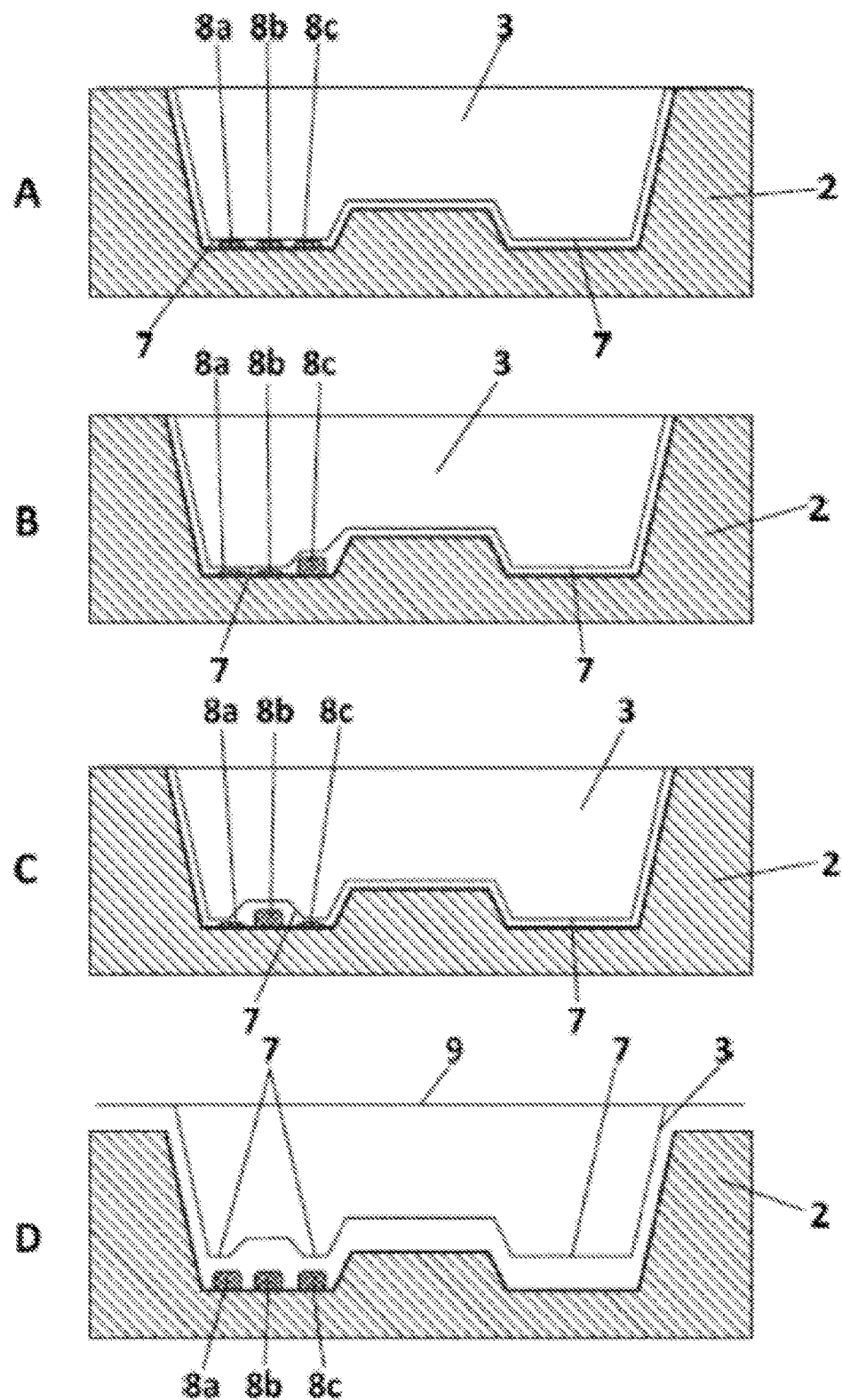
FIG. 2.—shows in a cross-sectional view, three alternative designs for the container.

FIG. 2 shows three designs alternatives for the container (3), which is configured as a receptacle having a bottom base, a side face and an open base. The bottom base has some protrusions (7) arranged at specific areas, such as by using this shape information as a code, the temperature and time settings of the device can be set.

The shape detection can be implemented by a plurality of switches (8) strategically located in the casing (2) to be activated by the inserted container, such as a binary code is generated from the container shape depending of what switches (8) has been activated. In the example of FIG. 2, three switches (8a,8b,8c) are provided on a surface of the casing (2) such a binary code of three digits can be generated, and depending on the shape of a part of the container (3), some of them would be pushed-down (activated).

In drawing 2A, the container (3) has a wide protrusion (7) in correspondence with the switches, and this protrusion is configured as to activate the three switches (8a,8b,8c). The container (3) of FIG. 2B has a protrusion (7) configured to activate switches (8a,8b), and the container (3) of FIG. 2C has a protrusion (7) configured to activate switches (8a,8c).

This detection switches may consist of end of run switches or lineal displacement sensor where the displacement value is a code representing temperature and timing settings.

Once a specific type of refill is detected, the control means executing an associated heating program for the detected refill, such as the temperature and activation time of the heating means will be controlled in accordance with that program.

In other preferred embodiments, optical detection means are additionally provided to the detected level of volatile substance inside the container.

Some advantages of the invention can be summarized as follows:
Optimal fragrance design from business perspective, cost variable temperature
Refills with different lifetime depending use, i.e. 4 hours or 8 hours, or any other time frame
Allow for versions with different durations,
Automatic stop by a timer or by detected fragrance End Of Life
Implement a burst mode to give a quick room fill on starup
No energy waste on heating empty refill
No waste of fragrance as the device runs until refill is empty.

The invention claimed is:

1. An electric dispensing device, the electric device comprising:
a casing comprising a first electric switch and a second electric switch;
a heater arranged in the casing;
a controller configured to control operation of the heater in accordance with a heating program selected from at least two heating programs; and
the controller is adapted to select for execution a first heating program of the at least two heating programs in response to activation of the first electric switch by at least one protrusion of a first container containing a first volatile substance when the first container is detachably coupled with the casing, and to select for execution a second heating program of the at least two heating programs in response to activation of the second electric switch by a second protrusion of a second container containing a second volatile substance when the second container is detachably coupled with the casing,
wherein the casing detachably couples to either the first container or the second container at any given time,
wherein the at least one protrusion of the first container activates the first electric switch but does not activate the second electric switch when the first container is detachably coupled with the casing,
wherein the second protrusion of the second container is different from the at least one protrusion of the first container, and activates the second electric switch but does not activate the first electric switch when the second container is detachably coupled with the casing,
wherein a first heating program from the at least two heating programs controls temperature and timing of the heater for the first volatile substance, and a second heating program from the at least two heating programs controls temperature and timing of the heater for the second volatile substance, and
wherein the first and second volatile substances are different.

2. The device according to claim 1, wherein each electric switch is an end of run switch.

3. The device according to claim 1, wherein the first container is configured as a receptacle comprising a bottom base, a side face and an open base, and
wherein the bottom base comprises the at least one protrusion arranged to activate the first electric switch.

4. The device according to claim 3, wherein each container has a vapor-permeable membrane covering the receptacle open base.

5. The device of claim 1, wherein the casing comprises a third electric switch configured to be activated by the at least one protrusion.

6. The device of claim 1, wherein, when activated, an upper surface of the first electric switch is at a first level relative to the casing, and an upper surface of the second electric switch is positioned at a second level relative to the casing, the second level being higher, with respect to a bottom of the casing, than the first level.

7. The device of claim 1, further comprising a metallic heat-sink configured to receive one of the containers.

8. The device according to claim 1, wherein each electric switch is a lineal displacement switch with a displacement value representing the temperature and the timing of the heater.

9. An electric dispensing device, the electric device comprising:
   a casing comprising a first electric switch, a second electric switch and a third electric switch;
   a heater arranged in the casing;
   a controller configured to control operation of the heater in accordance with a heating program selected from a plurality of heating programs; and
   the controller is configured:
      to select for execution a first heating program of the plurality of heating programs in response to activation of the first electric switch by a first protrusion of a first container containing a first volatile substance when the first container is detachably coupled with the casing, and
      to select for execution a second heating program of the plurality of heating programs that is different from the first heating program in response to activation of the second electric switch by a second protrusion of a second container containing a second volatile substance when the second container is detachably coupled with the casing,
   wherein the casing detachably couples to either the first container or the second container at any given time,
   wherein the at least one protrusion of the first container activates the first electric switch but does not activate the second electric switch when the first container is detachably coupled with the casing,
   wherein the second protrusion of the second container is different from the at least one protrusion of the first container, and activates the second electric switch but does not activate the first electric switch when the second container is detachably coupled with the casing,
   wherein the first heating program from the plurality of heating programs controls temperature and timing of the heater for the first volatile substance, and the second heating program from the plurality of heating programs controls temperature and timing of the heater for the second volatile substance, and
   wherein the first and second volatile substances are different.

10. The device of claim 9, further comprising a metallic heat-sink configured to receive one of the containers.

11. The device according to claim 9, wherein each electric switch is a lineal displacement switch with a displacement value representing the temperature and the timing of the heater.

* * * * *